US011793904B2

(12) United States Patent
Rasansky et al.

(10) Patent No.: US 11,793,904 B2
(45) Date of Patent: Oct. 24, 2023

(54) PROTECTIVE RESPIRATOR UTILIZING FAR UV-C IRRADIATION

(71) Applicant: XCMR Inc., Narberth, PA (US)

(72) Inventors: Richard A. Rasansky, Narberth, PA (US); Kenneth Kelley, Menlo Park, CA (US)

(73) Assignee: XCMR, Inc., Narberth, PA (US)

( * ) Notice: Subject to any disclaimer, the term of this patent is extended or adjusted under 35 U.S.C. 154(b) by 0 days.

(21) Appl. No.: 17/644,041

(22) Filed: Dec. 13, 2021

(65) Prior Publication Data

US 2022/0184267 A1 Jun. 16, 2022

Related U.S. Application Data

(60) Provisional application No. 63/265,336, filed on Dec. 13, 2021, provisional application No. 63/124,437, filed on Dec. 11, 2020.

(51) Int. Cl.
*A61L 9/20* (2006.01)
*A62B 7/00* (2006.01)

(52) U.S. Cl.
CPC ....... *A61L 9/20* (2013.01); *A62B 7/00* (2013.01); *A61L 2209/111* (2013.01)

(58) Field of Classification Search
CPC .. A61L 9/20; A61L 2209/111; A61L 2209/14; A62B 7/00
See application file for complete search history.

(56) References Cited

U.S. PATENT DOCUMENTS

| 8,733,356 | B1 | 5/2014 | Roth |
| 2010/0028201 | A1 | 2/2010 | Neister |
| 2011/0272595 | A1 | 11/2011 | Neister |
| 2014/0140888 | A1 | 5/2014 | Neister |
| 2014/0227132 | A1 | 8/2014 | Neister |

(Continued)

FOREIGN PATENT DOCUMENTS

WO 2007084145 A2 7/2007

OTHER PUBLICATIONS

Ahmed, et al., Ray Tracing for Fluence Rate Simulations in Ultraviolet Photoreactors, 52 Environ. Sci. Technol. 4738 (2018).

(Continued)

*Primary Examiner* — Sean E Conley
*Assistant Examiner* — Brendan A Hensel
(74) *Attorney, Agent, or Firm* — Blank Rome LLP

(57) ABSTRACT

A protective respirator that deactivates pathogens in a kill zone in front of a mouth and nose of a user by emitting Far UV-C radiation (e.g., having a wavelength centered around 222 nanometers). In some embodiments, a controller uses a mathematical model to determine a required intensity or emission time to provide a threshold probability of killing a microbe (e.g., a virus such as SARS-CoV-2). The required intensity or time may be determined based on atmospheric conditions and/or physiological conditions of the user. The Far UV-C radiation may be emitted in a direction through the kill zone that does not intersect with the skin or eyes of the user (e.g., away from the user or across the front of the user's face). Alternatively, the controller may estimate the fluence of Far UV-C radiation at the skin or eyes of the user over time and adjust the Far UV-C radiation emitted.

19 Claims, 14 Drawing Sheets

(56) References Cited

U.S. PATENT DOCUMENTS

2018/0353629 A9  12/2018  Neister et al.

OTHER PUBLICATIONS

Ahmed, et al., Stochastic Evaluation of Disinfection Performance in Large-Scale Open-Channel UV Photoreactors, 145 J. Environ. Eng. 04019071 (2019).

Blatchley, et al., Far UV-C Radiation: Current State-of-Knowledge, International Ultraviolet Association (2021).

Blatchley, et al., SARS-CoV-2 Ultraviolet Radiation Dose-Response Behavior. 126 Journal of Research of the National Institute of Standards and Technology 126018 (2021).

Buonanno, et al., Germicidal Efficacy and Mammalian Skin Safety of 222-nm UV Light, 187 Radiation Research 493 (2017).

Buonanno, et al., Far-UVC light (222 nm) efficiently and safely inactivates airborne human coronaviruses, 10 Scientific Reports 10285 (2020).

Chiu, et al., Effect of UV system modifications on disinfection performance, 125 J. Environ. Eng. 459 (1999).

Chiu, et al., Integrated UV disinfection model based on particle tracking. 125 J. Environ. Eng. 1 (1999).

Davey, et al., Heat stress and PPE during COVID-19: impact on healthcare workers' performance, safety and well-being in NHS settings, 108 J. Hospital Infection 185 (2021).

Eden, et al., Microcavity and Microchannel Plasmas: General Characteristics and Emerging Applications, Complex Plasmas (2014), M. Bonitz et al. (eds.), pp. 373-398.

Eden, et al., Microcavity plasma devices and arrays: a new realm of plasma physics and photonic applications, 47 Plasma Phys. Control. Fusion B83 (2005).

Editorial, "Emerging zoonoses: A one health challenge," 19 EClinicalMedicine 100300 (2020).

EPA Office of Water, Ultraviolet Disinfection Guidance Manual for the Final Long Term 2 Enhanced Surface Water Treatment Rule, EPA 815-R-06-007 (2006).

Fukui, et al., Exploratory clinical trial on the safety and bactericidal effect of 222-nm ultraviolet C irradiation in healthy humans, PLoS One 15(8): e0235948.

Howe, How far-UVC technology can help attractions battle against Covid-19, Blooloop, Nov. 12, 2020, https://blooloop.com/technology/in-depth/far-uvc-technology-attractions-covid-19/.

Jenny, et al., Heuristic optimization of a continuous flow point-of-use UV-LED disinfection reactor using computational fluid dynamics. 83 Water Research 310 (2015).

Jenny, et al., Modeling a continuous flow ultraviolet Light Emitting Diode reactor using computational fluid dynamics. 116 Chem Eng. Sci. 524 (2014).

Jin, et al., Impact of lamp shadowing and reflection on the fluence rate distribution in a multiple low-pressure UV lamp array, 39 Water Research 2711 (2005).

Kariwa, et al., Inactivation of SARS coronavirus by means of povidone-iodine, physical conditions, and chemical reagents, 212 Dermatology 119 (2006).

Li, M.K., et al., On-Site Determination and Monitoring of Real-Time Fluence Delivery for an Operating UV Reactor Based on a True Fluence Rate Detector, 51 Environ. Sci. Technol. 8094 (2017).

Li, M.K., et al., Experimental Evaluation of Turbidity Impact on the Fluence Rate Distribution in a UV Reactor Using a Microfluorescent Silica Detector. 51 Env. Sci. Technol. 13241 (2017).

Li, M.K., et al. Experimental Assessment of Photon Fluence Rate Distributions in a Medium-Pressure UV Photoreactor, 51 Env. Sci. Technol. 3453 (2017).

Li, M.K., et al. In Situ Measurement of UV Fluence Rate Distribution by Use of a Micro Fluorescent Silica Detector. 45 Env. Sci. Technol. 3034 (2011).

Li, Y., et al., Probable airborne transmission of SARS-CoV-2 in a poorly ventilated restaurant, 196 Building and Environment 107788 (2021).

Lieberman, M. A., et al., Principles of plasma discharges and material processing, John Wiley & Sons, N.Y., 2005.

Liu, et al., Evaluation of alternative fluence rate distribution models. 53 J. Water Supply Research Technol. 391 (2004).

Lyn, Steady and unsteady simulations of turbulent flow and transport in ultraviolet disinfection channels. 130 J. Hydraul. Eng. 762 (2004).

Lyn, et al., Numerical computational fluid dynamics-based models of ultraviolet disinfection channels, 125 J. Environ. Eng. 17 (2005).

Madhav, et al., Pandemics: Risks, Impacts, and Mitigation, Disease Control Priorities: Improving Health and Reducing Poverty (3rd ed), vol. 9, World Bank Group (2018).

Parush, Human Factor Considerations in Using Personal Protective Equipment in the COVID-19 Pandemic Context Binational Survey Study, 22 J. Med. Internet Res. e19947 (2020).

Raeiszadeh, et al., Microplasma UV lamp as a new source for UV-induced water treatment: Protocols for characterization and kinetic study, 164 Water Research 114959 (2019).

Ruskin, et al., "COVID-19, Personal Protective Equipment, and Human Performance," 134 Anesthesiology 518 (2021).

Jung, et al., Demonstration of Antiviral Activity of Far-UVC Microplasma Lamp Irradiation against SARS-CoV-2, 67 Clin. Lab. (2021).

Zhang, et al., Identifying airborne transmission as the dominant route for the spread of COVID-19, 117 PNAS 14857 (2020).

Capatillo, et al., Computational fluid dynamics analysis to assess performance variability of in-duct UV-C systems, 21 Sci. Technol. Built Env. 45 (2015).

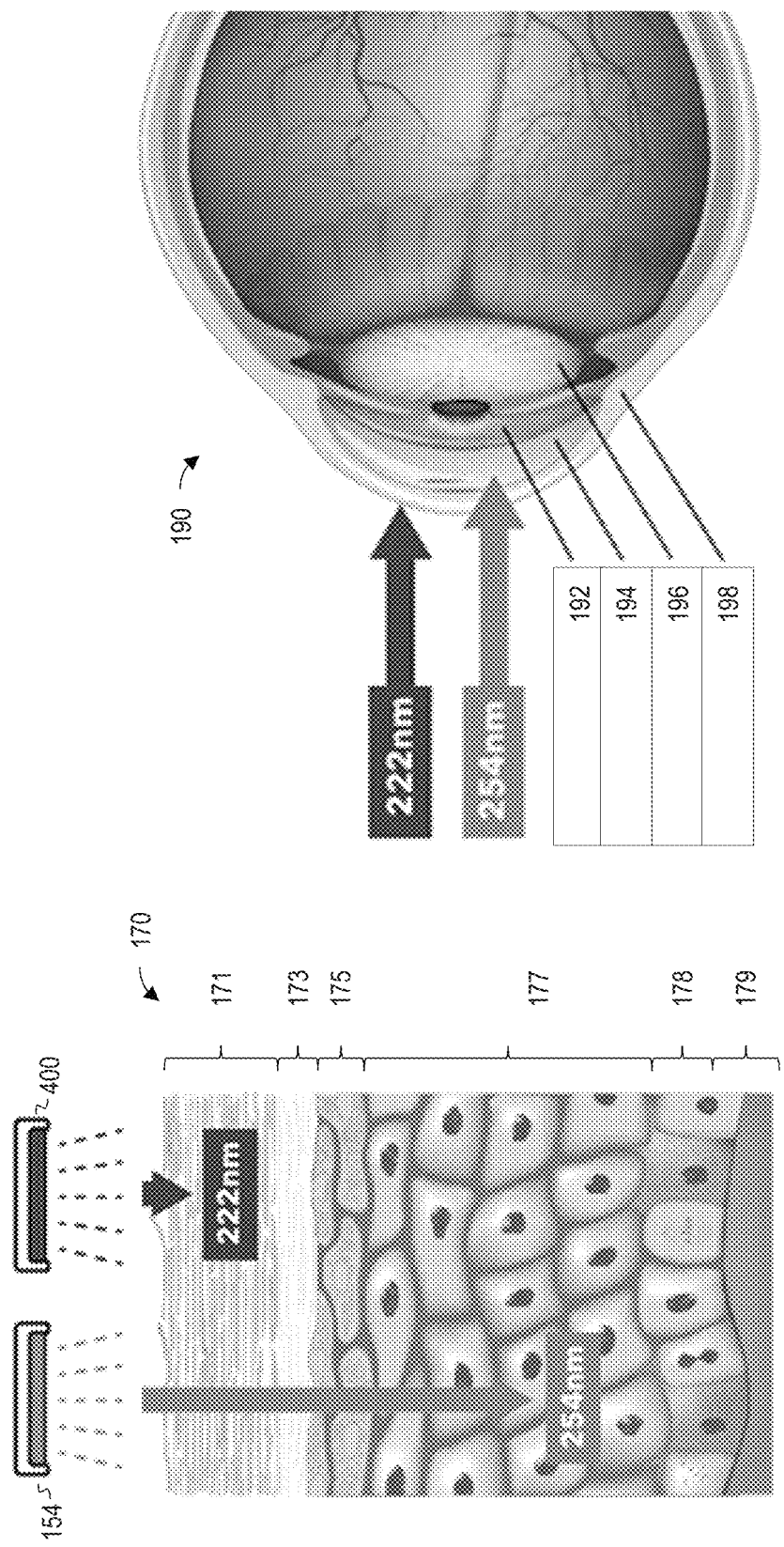

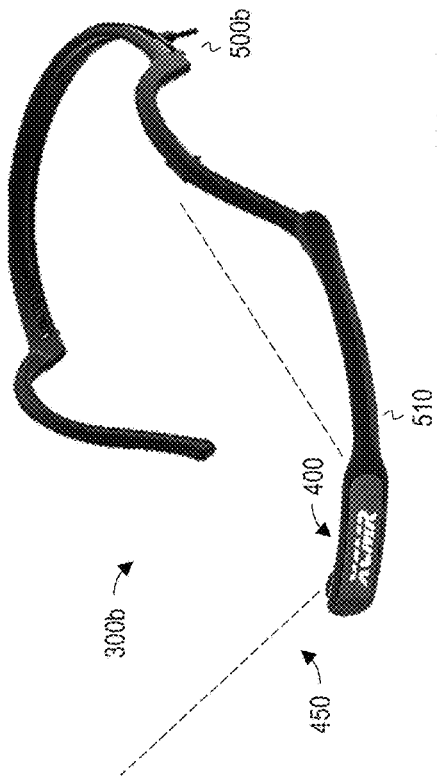
FIG. 5B
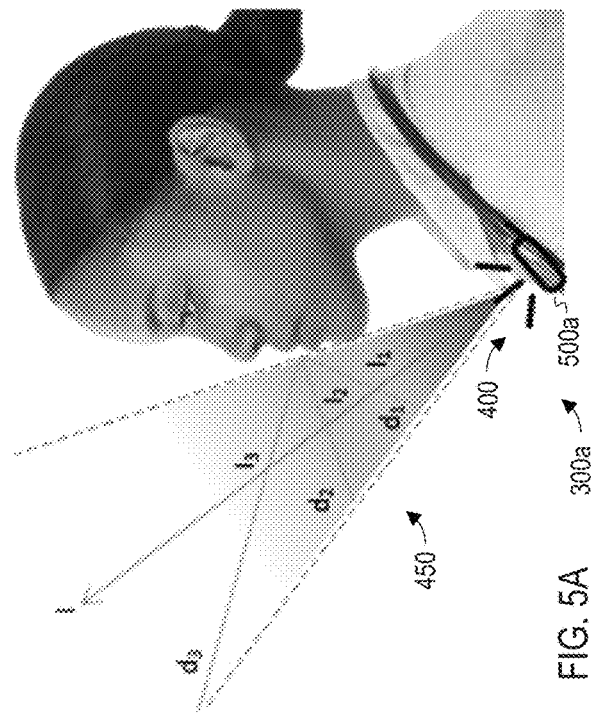
FIG. 5A
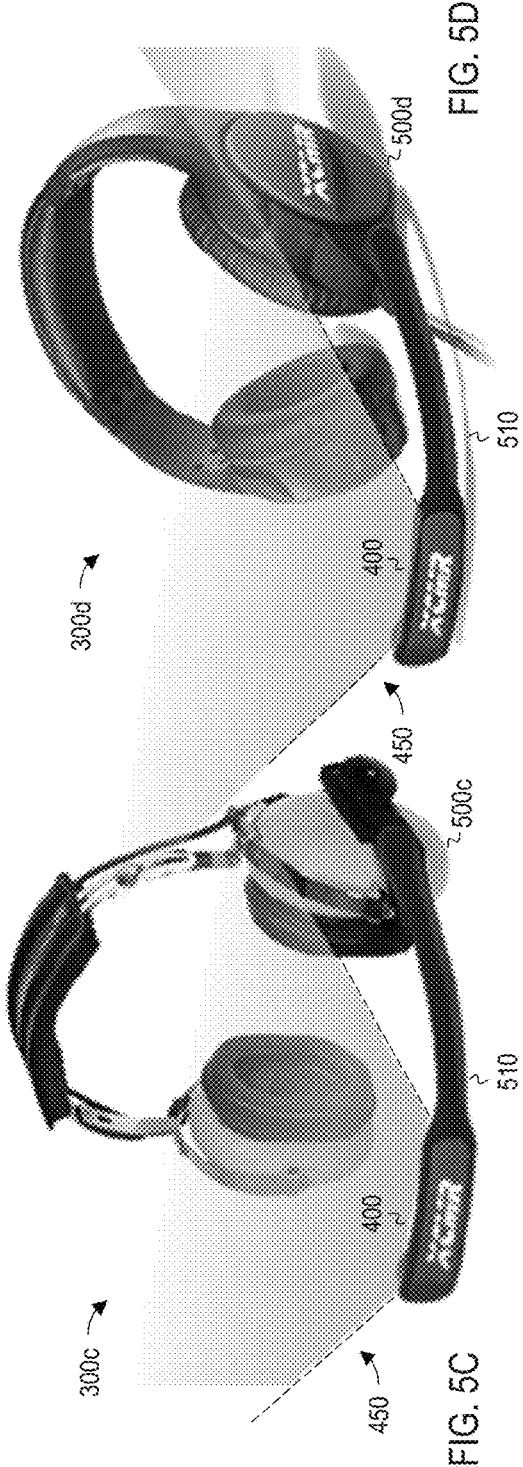
FIG. 5D
FIG. 5C

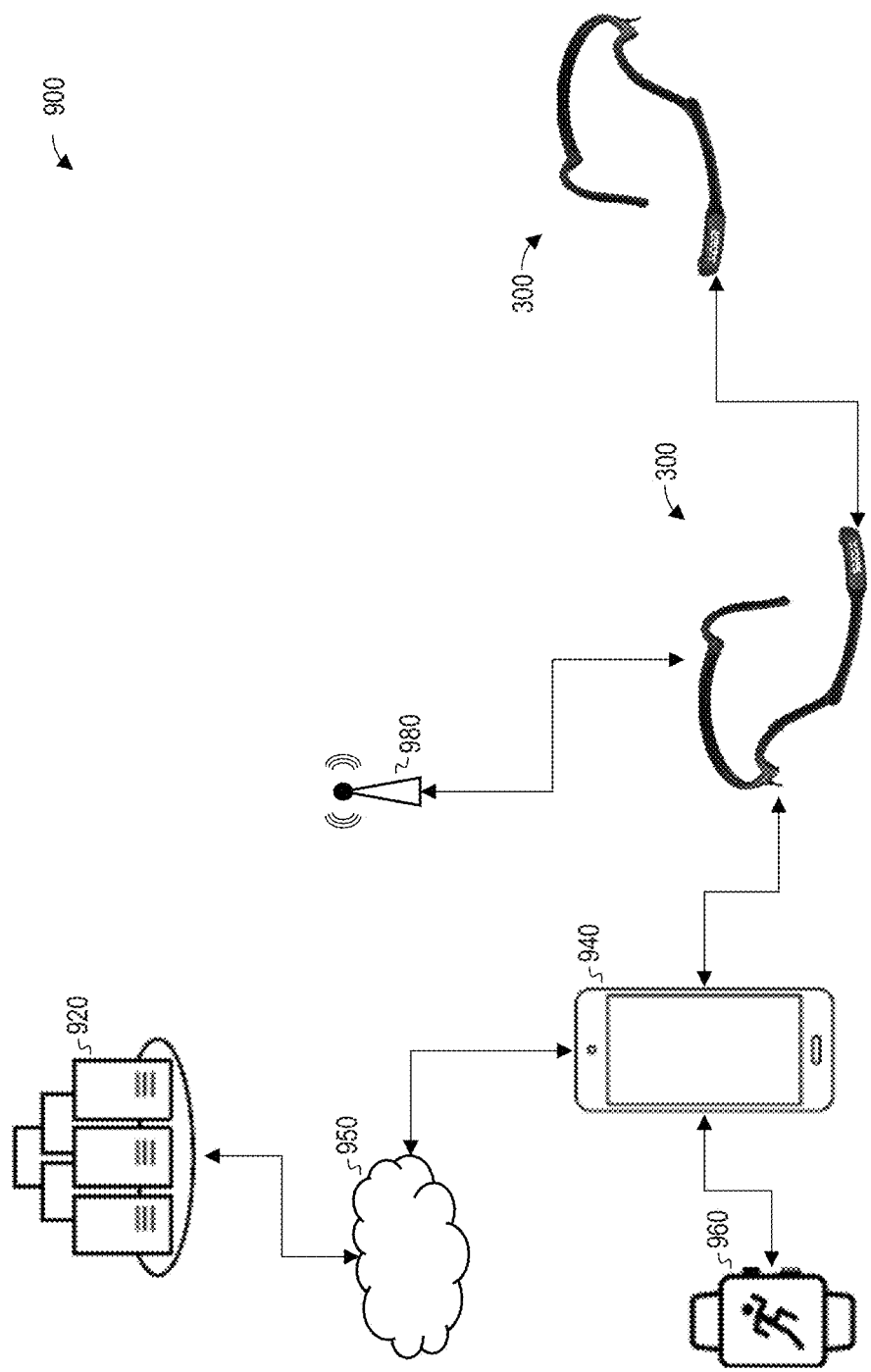

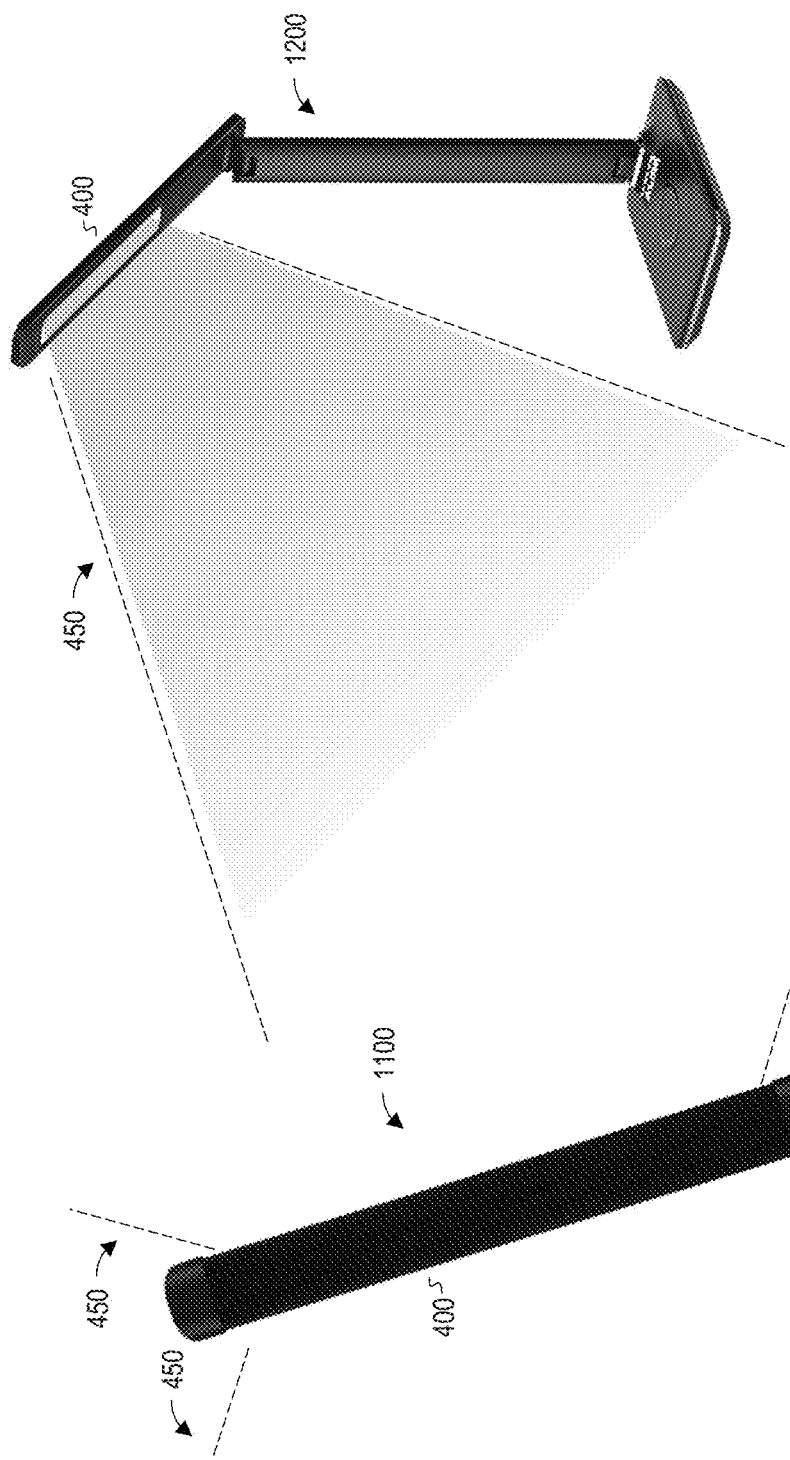

PROTECTIVE RESPIRATOR UTILIZING FAR UV-C IRRADIATION

CROSS-REFERENCE TO RELATED APPLICATIONS

This application claims priority to U.S. Prov. Pat. Appl. No. 63/124,437, filed Dec. 11, 2020, and U.S. Prov. Pat. Appl. No. 63/265,336, filed Dec. 13, 2021, which are hereby incorporated by reference.

FEDERAL FUNDING

None

BACKGROUND

Over the past decade, natural pandemics of influenza, Zika, and coronaviruses have caused economic destruction and morbidity and mortality across the globe. Natural pandemics are likely to recur based on zoonotic outbreaks as evidenced over the past decade (e.g., H1N1, SARS, MERS, Zika, Ebola, Marburg) as well as increasing size of vulnerable populations, new vulnerable birth cohorts every year, and elderly people experiencing immuno-senescence. COVID-19 illustrated the gravity of biological threats, especially to the United States, given its inadequate preparations and means of response.

By definition, novel biological threats have no proven vaccines or medicines, requiring reliance only on public health measures like personal hygiene, physical separation, decontamination of surfaces and air, and the donning of personal protective equipment (PPE) such as masks, gloves and goggles. The stockpiling and provision of disposable PPE, hand sanitizers, and air filters was shown to be extremely challenging in the COVID-19 pandemic. Yet the dramatic increase in the use of PPE (of varying quality from high filtration N-95 and KN-95 masks to home-made cotton cloth masks) likely contributed to the significant decrease in the seasonal influenza incidence and prevalence in 2020-2021 and initial 2021-2022 seasons.

Highly effective PPE, such as N95-type masks, are often single use objects worn for a short duration. Meanwhile, N95-type masks are often poorly utilized due to discomfort and poor fitting. Additionally, when scaled to meet global demand, single use objects are an expensive solution. Accordingly, effective, re-usable, scalable PPE is needed to address respiratory pathogens such as influenza, coronaviruses, respiratory syncytial virus (RSV), human Metapneumovirus (HMPV), and others. Those respiratory viruses are the leading cause of illness and death from communicable respiratory disease.

Ultraviolet (UV) radiation having a wavelength between about 200 nanometers (nm) and 320 nm causes photochemical damage to critical biomolecules like deoxyribonucleic acid (DNA) and ribonucleic acid (RNA). Therefore, UV radiation in the 200-320 nm range, which is sometimes referred to as "germicidal UV," can be used to disinfect surfaces and volumes of air. UV radiation having a wavelength less than about 240 nm also damages proteins, which can also lead to microbial and viral inactivation. Extended exposure to radiation from a portion of the UV spectrum, however, can cause damage to human skin and eyes. Accordingly, to take advantage of the disinfectant properties of germicidal UV irradiation, there is a need to protect human tissue from prolonged exposure to radiation having a wavelength in the portion of the spectrum where the radiation can damage human tissue.

SUMMARY

A protective respirator that provides "near field" protection for a user by emitting Far UV-C radiation (e.g., having a wavelength centered around 222 nanometers) through a kill zone in front of a mouth and nose of a user. In embodiments, the protective respirator includes a power source, one or more Far UV-C radiation sources that emit Far UV-C radiation, and a controller that uses a mathematical model to determine a required intensity of the Far UV-C radiation or a required time to emit the Far UV-C radiation to provide a threshold probability of killing a microbe (e.g., a virus such as SARS-CoV-2) traveling through the kill zone. The mathematical model is developed by using computational fluid dynamics to combine velocity fields in simulated environments, the fluence of the Far UV-C radiation emitted by Far UV-C radiation source(s), and the intrinsic kinetics of the inactivation response of the microbe identified using laboratory experiments.

Because the required intensity or time may be dependent on atmospheric conditions, in some embodiments the controller receives data indicative of the one or more atmospheric conditions. In some embodiments, the data is determined by one or more atmospheric sensors. In some embodiments, the data is received from a server, a personal electronic device, or a location beacon.

Because those atmospheric conditions may be dependent on one or more physiological conditions of the user, in some embodiments the controller receives data indicative of one or more physiological conditions of the user. In some embodiments, the data is determined by an inertial measurement unit, a geolocation module, or one or more physiological sensors. In some embodiments, the data is received from a personal electronic device or a fitness tracker.

In some embodiments, the Far UV-C radiation source(s) emit the Far UV-C radiation away from the user. In some embodiments, the Far UV-C radiation source(s) emit the Far UV-C radiation through the kill zone in a direction that does not intersect with the skin or eyes of the user. In other embodiments, the controller estimates the fluence of Far UV-C radiation at the skin or eyes of the user over time and adjusts the Far UV-C radiation emitted by the one or more Far UV-C radiation sources in response to the determination.

In some embodiments, the controller monitors a charge level of the power source over time adjusts the Far UV-C radiation emitted by the one or more Far UV-C radiation sources in response to the determination.

BRIEF DESCRIPTION OF THE DRAWINGS

Aspects of exemplary embodiments may be better understood with reference to the accompanying drawings. The components in the drawings are not necessarily to scale, emphasis instead being placed upon illustrating the principles of exemplary embodiments.

FIG. 1A is a diagram of ultraviolet (UV) penetration into human skin;

FIG. 1B is a diagram of UV penetration into a human eye;

FIG. 5A illustrates the protective respirator according to a wearable embodiment;

FIG. 5B illustrates the protective respirator according to another wearable embodiment;

FIG. 5C illustrates the protective respirator according to another wearable embodiment;

FIG. 5D illustrates the protective respirator according to another wearable embodiment;

FIG. 9 is a diagram of a network environment according to exemplary embodiments;

FIG. 11 illustrates the protective respirator according to a portable embodiment; and FIG. 12 illustrates the protective respirator according to a stationary embodiment.

DETAILED DESCRIPTION

Figure 2A:
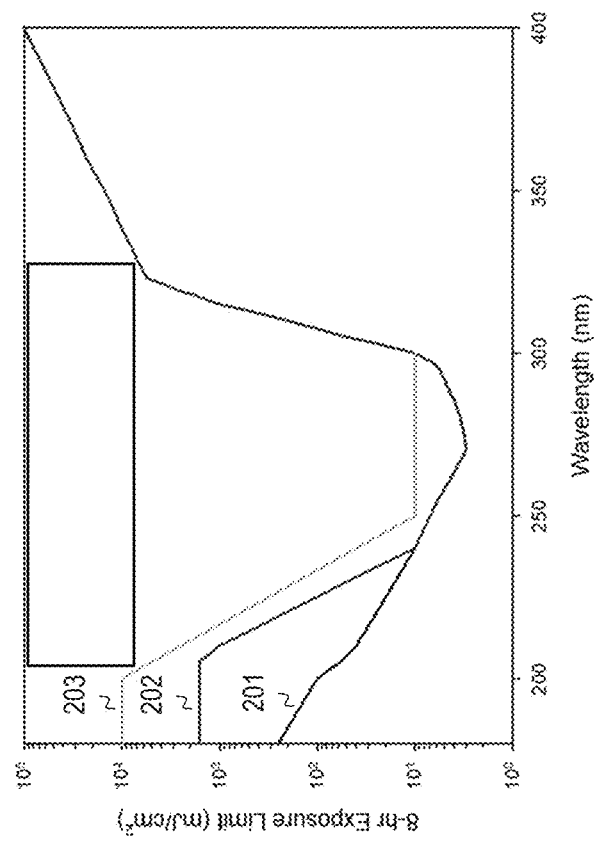
FIG. 2A is a graph of the relative spectral effectiveness of UV radiation as a function of wavelength

Reference to the drawings illustrating various views of exemplary embodiments is now made. In the drawings and the description of the drawings herein, certain terminology is used for convenience only and is not to be taken as limiting the embodiments of the present invention. Furthermore, in the drawings and the description below, like numerals indicate like elements throughout.

While some ultraviolet (UV) radiation causes damage to human tissue, recent research has shown that UV radiation having a wavelength between about 200 nanometers (nm) and 230 nm (informally referred to as "Far UV-C" radiation) causes minimal damage to critical mammalian tissues, including the skin and eyes.

FIG. 1A is a diagram of UV penetration into human skin 170, which includes the stratum corneum (dead layer) 171, the stratum lucidum 173, the stratum granulosum (granular layer) 175, the stratum spinosum (spinous later) 177, the stratum basale (basal layer) 178, and the dermis 179. As shown in FIG. 1A, radiation from a 254 nm source 154 can penetrate through the stratum corneum 171, the stratum lucidum 173, and the stratum granulosum 175 until it is absorbed by the stratum spinosum 177. By contrast, however, radiation from a 222 nm source 400 is almost completely absorbed in the stratum corneum, the outer layer of dead cells in human skin 170.

FIG. 1B is a diagram of UV penetration into a human eye 190, which includes the iris 192, aqueous humor 194, the lens 196, and the cornea 198. As shown in FIG. 1B, 222-nm radiation does not penetrate beyond a layer of dead cells on the outside surface of the cornea 198. Because Far UV-C radiation is only absorbed by dead cells within human skin and eyes, it causes little or no damage to those tissues. Recent experiments involving mammalian models (hairless mice) and human tissues support these conclusions.

To protect human beings, organizations including the American Conference of Governmental Industrial Hygienists (ACGIH) and the International Commission on Non-Ionizing Radiation Protection (ICNIRP) establish threshold limit values (TLVs), which are recommended limits of exposure to each harmful substance or thing that a person can be exposed to without adverse health effects. The recent research demonstrating the safety of Far UV-C radiation prompted reevaluation of the exposure limit for Far UV-C radiation.

FIG. 2A is a graph of the relative spectral effectiveness of UV radiation as a function of wavelength (on the horizontal axis). As shown in FIG. 2A, the potential for UV irradiation to cause damage to human tissue peaks at about 270 nm. At longer wavelengths, radiation becomes insufficiently energetic to cause damage. At shorter wavelengths, it fails to penetrate to the germinative layers that spawn new cells. These values of spectral effectiveness are then used to identify daily (8 hour) exposure limits (that of a typical work day for laborers).

Figure 2B:
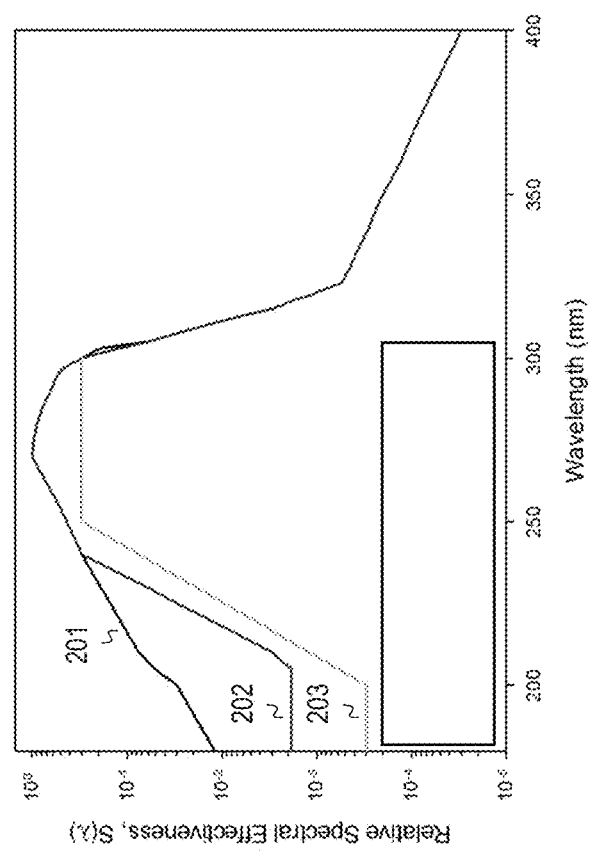
FIG. 2B is a graph of the threshold limit values as a function of wavelength.

FIG. 2B is a graph of the threshold limit values in millijoules per square centimeter ($mJ/cm^2$) as a function of wavelength. Lines 201 are the current guidance provided by the ACGIH and the ICNIRP. Lines 202 and 203 are proposed updated guidance to the threshold limit values (TLVs) for exposure of human skin (line 203) and eyes (line 202) in view of recent research findings. These proposed changes to the 8-hour exposure limits represent a 7-fold increase for allowable exposure to the eyes (from 23 $mJ/cm^2$ to 161 $mJ/cm^2$) and more than a 20-fold increase for allowable exposure to the skin (from 23 $mJ/cm^2$ to 479 $mJ/cm^2$).

As described above, exposure to Far UV-C radiation has been shown to be significantly safer for human tissue than was previously assumed. Meanwhile, Far UV-C irradiation remains effective for disinfection. In fact, because respiratory viruses (including SARS-CoV-2, HuCoV-229E, and Influenza A) are among the most sensitive pathogens to Far UV-C radiation, inactivating respiratory viruses requires very low doses of Far UV-C radiation. Because the exposure limits recently proposed by the ACGIH far exceed the doses of Far UV-C radiation that are likely to be required in disinfection applications, Far UV-C irradiation can be safely used to inactivate pathogens in air, in aerosols, on surfaces, or in water. Therefore, protective respirators and devices are disclosed that take advantage of the safety and efficacy of Far UV-C irradiation to provide effective, re-usable, and scalable personal protection for individuals and groups of individuals.

Figure 3:
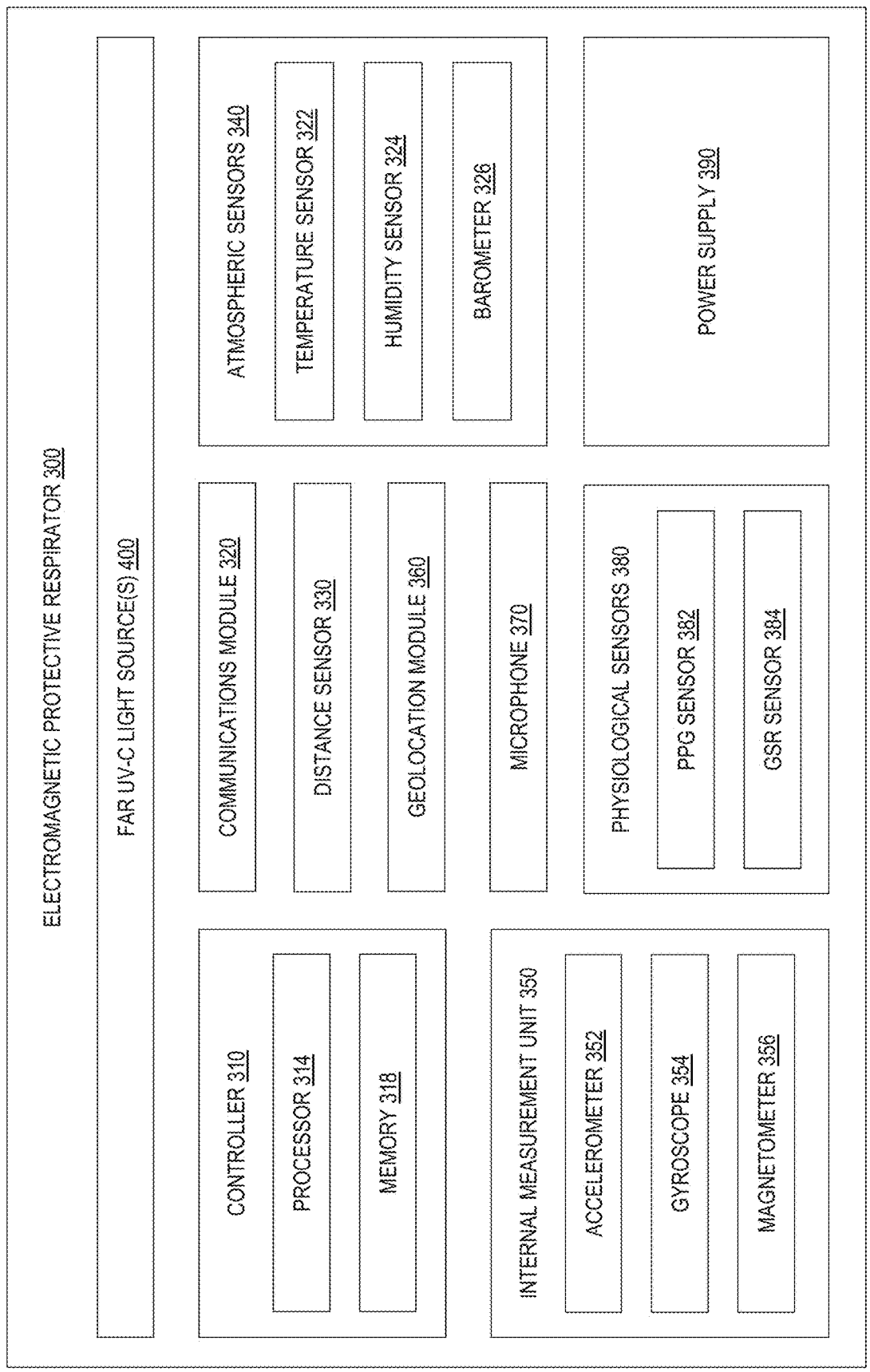
FIG. 3 is a block diagram of a protective respirator according to exemplary embodiments.

FIG. 3 is a block diagram of a protective respirator 300 according to exemplary embodiments. As shown in FIG. 3, the protective respirator 300 includes one or more Far UV-C radiation sources 400, a controller 310, and a power supply 390. In some embodiments, the protective respirator 300 may also include a proximity sensor 320, a communications module 320, atmospheric sensors 340, an inertial measurement unit 350, a geolocation module 360, a microphone 370, and/or physiological sensors 380.

The Far UV-C radiation source(s) 400 may include any source of UV radiation having a wavelength between about 200 nm and about 230 nm. As described below with reference to FIG. 4, the Far UV-C radiation sources 400 may be optically-filtered krypton-chloride (KrCl*) excimer lamps that outputs Far UV-C radiation having a wavelength centered around 222 nm.

The controller 310 may be any suitable computing device capable of performing the functions described herein. In the embodiment of FIG. 3, the controller 310 includes non-transitory computer readable storage media (memory 318) and a hardware computer processor 314. In other embodiments, the controller 310 may be, for example, a finite state machine.

The communications module 320 may be any hardware device enabling the protective respirator 300 to communicate with other electronic devices directly and/or via a network. For example, the communications module 320 may provide functionality for the respirator 300 to communicate with other respirators 300 and/or personal electronic devices (e.g., smartphones, activity monitors, fitness trackers, etc.) using direct, short range, wireless communication (e.g., Bluetooth).

The distance sensor 330 may be any device suitably configured to detect the presence of nearby objects without any physical contact and sense data indicative of the distance between the protective respirator 300 and the nearby object.

The atmospheric sensors 340 may include any electronic device used to collect data indicative of the atmosphere surrounding protective respirator 300. The atmospheric sensors 340 may include a temperature sensor 322, a relative humidity sensor 324, a barometer 326, and/or a wind speed sensor 328.

The inertial measurement unit 350 may include any hardware device that measures and reports the motion and/or orientation of the protective respirator 300. The internal measurement unit 350 may include an accelerometer 352, a gyroscope 354, and/or a magnetometer 356.

The geolocation module 360 may include any hardware device that determines or estimates the geographic position of the protective respirator 300 using, for example, satellite navigation, network identification, communication with location beacons, etc.

The microphone 370 may be any hardware device that senses audible noise. The power supply 390 may be any hardware device that provides electrical power to the protective respirator 300. In the wearable embodiments described below, the power supply 390 may be a rechargeable battery. In other embodiments, the power supply 390 may be a wired connection to an external power source.

The physiological sensors 380 may include any hardware device that senses data indicative of the physiological condition of a user wearing the protective respirator 300. The physiological sensors 380 may include a photoplethysmogram (PPG) sensor 382, which uses a light source and a photodetector at the surface of skin to measure the volumetric variations of blood circulation, and/or a galvanic skin response (GSR) sensor 384, which detects the changes in electrical (ionic) activity resulting from changes in sweat gland activity. Data from the PPG sensor 382 may be used, for example, to estimate frequency, intensity, and amplitude of the user's respiration.

Motion of the protective respirator 300 may affect the data captured by the physiological sensors 380, the atmospheric sensors 340, etc. Therefore, in some embodiments, the controller 310 may determine the motion of the protective respirator 300 and use a digital signal processing algorithm (stored, for example, in the memory 318) to remove motion artifacts from the data received by the sensors that are affected by motion.

Figure 4A:
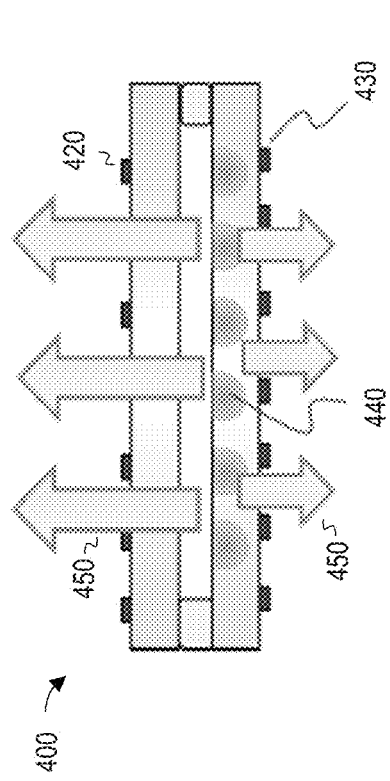
FIGS. 4A and 4B are diagrams of a Far UV-C radiation source according to an exemplary embodiment.
Figure 4B:
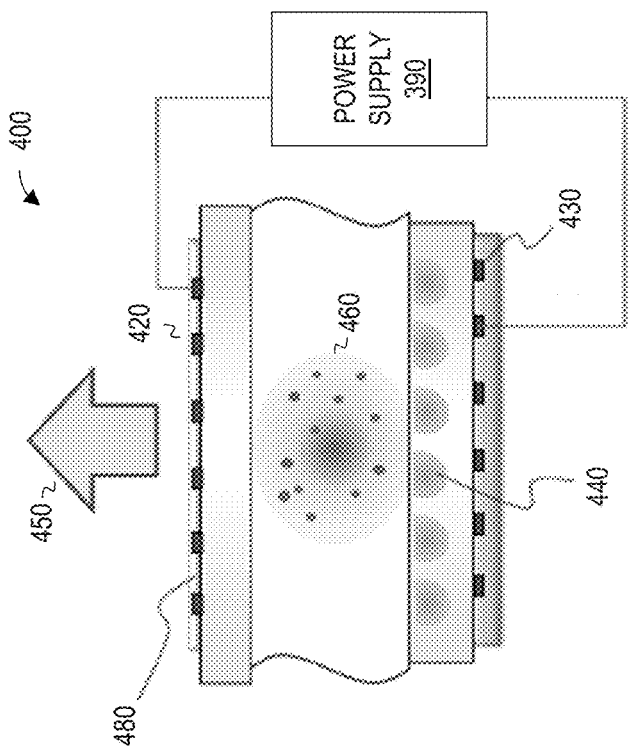

FIGS. 4A and 4B are diagrams of a Far UV-C radiation source 400 according to an exemplary embodiment.

In the embodiment of FIGS. 4A and 4B, the Far UV-C radiation source 400 includes a plurality of microcavities 440 that each store low temperature plasma. The Far UV-C radiation source 400 also includes a plurality of anodes 420 and cathodes 430 electrically connected to the power supply 390. In response to power supplied by the anodes 420 and cathodes 430, the plasma in the microcavities 440 generate excimers 460, which emit Far UV-C radiation 450. In the embodiment of FIGS. 4A and 4B, the excimers 460 are krypton chloride.

Figure 4C:
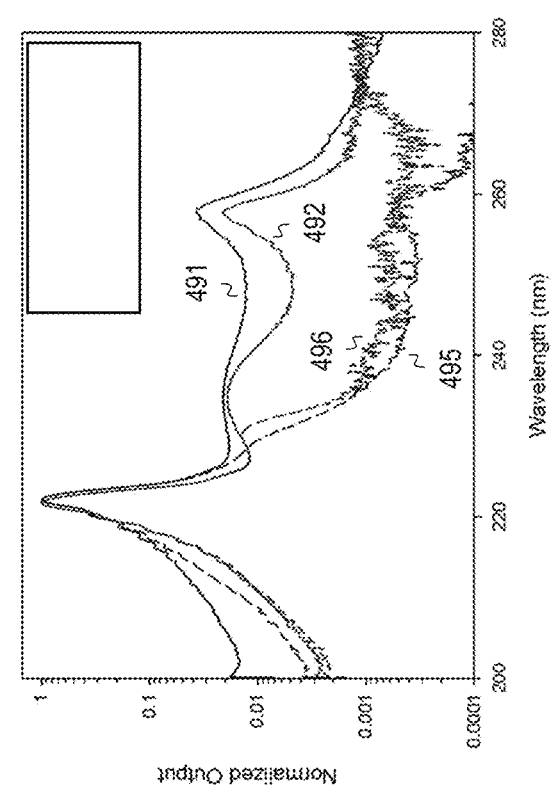
FIG. 4C is a graph of the normalized output of two exemplary Far UV-C radiation sources.

FIG. 4C is a graph 490 of the normalized output (on a logarithmic scale) of two exemplary Far UV-C radiation sources 400 across the UV spectrum. Line 491 represents the normalized output of a first exemplary Far UV-C radiation source 400 (without filtering) and line 492 represents the normalized output of a second exemplary Far UV-C radiation source 400 (without filtering). As shown in FIG. 4C, the krypton-chloride (KrCl*) excimer lamps have a dominant, primary peak centered around 222 nm and are therefore well suited for inactivation of aerosolized viruses as described below.

Krypton-chloride excimer lamps also have a secondary peak around 258 nm. Because radiation having a wavelength in the secondary peak has the potential to do damage to human tissue, the Far UV-C radiation sources 400 of FIGS. 4A and 4B also include an optical filter 480 to attenuate transmission outside the Far UV-C spectrum. In the graph 490, line 495 represents the optically-filtered output of the first exemplary Far UV-C radiation source 400 having the optical filter 480 and line 492 represents the normalized output of the second exemplary Far UV-C radiation source 400 Far UV-C radiation source 400 having the optical filter 480. As shown in the graph 490, when the optical filter 480 is applied it can reduce the potentially harmful secondary peak by a factor of approximately 100.

Known as a microcavity plasma (or simply, a microplasma), these exemplary Far UV-C radiation sources 400 are characterized by continuous operation at pressures up to and beyond one atmosphere, low gas temperatures, and plasma volumes in the nanoliter range. The confinement of the plasma by a cavity results in the production of a stable, diffuse and uniform glow discharge having an electron temperature of several eV and electron densities of $10^{13}$-$10^{16}$ cubic centimeters ($cm^3$). These values are unprecedented for a continuous wave (CW), high pressure glow and are ideally suited for the efficient excitation of optical emitters in the gas phase. Because of the unique characteristics of plasmas confined to the microcavity structures 440, the exemplary Far UV-C radiation sources 400 of FIGS. 4A and 4B are thin, lightweight UV radiation sources that provide instant illumination and de-illumination over a long lifespan.

Unbalanced photon flux (dosage) may lead to an inconsistent killing rate over a space or time period. Conventional UV lamps have a cylindrical geometry and are therefore not conducive to a uniform treatment over a large area without a specific fixture. In contrast, exemplary Far UV-C radiation sources 400 of FIGS. 4A and 4B efficiently utilize Far UV-C photons in a flat form factor, providing a uniform distribution of radiated photons over large scale surfaces or spaces to effectively kill microbes and viruses over the target space (air, aerosols, particles, droplets, surfaces, water etc.).

As described above with reference to FIGS. 4A and 4B, in some embodiments, the Far UV-C radiation source(s) 400 may be microplasma krypton-chloride excimer lamps. However, in other embodiments, the protective respirator 300 may include other Far UV-C radiation source(s) 400, including excimer lasers, light emitting diodes (LEDs), laser diodes, etc.

Figure 5F:
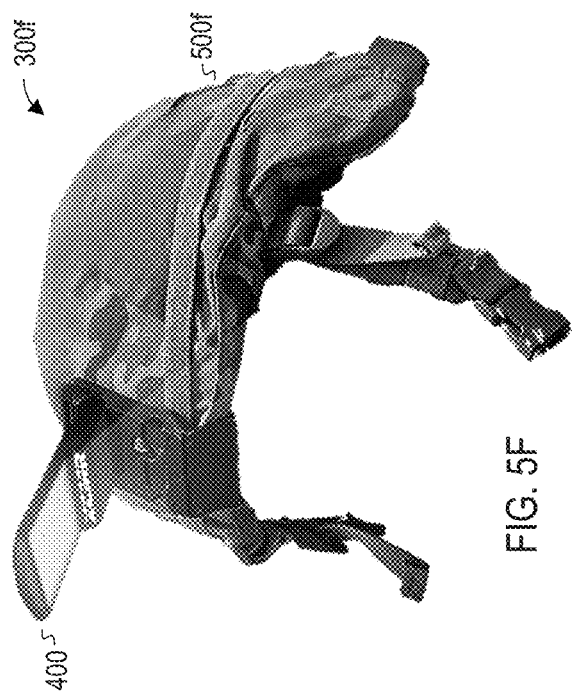
FIG. 5F illustrates the protective respirator according to another wearable embodiment.

FIGS. 5A through 5G illustrate protective respirators 300 according to various wearable embodiments. In the embodiment of FIG. 5A, the protective respirator 300a is realized such that the Far UV-C radiation source(s) 400 are incorporated in a pendant 500a that can be worn around the neck of the user to emit Far UV-C radiation 450 through a volume in front of the user's nose and mouth, effectively covering the volume of respiration of the individual.

Figure 5E:
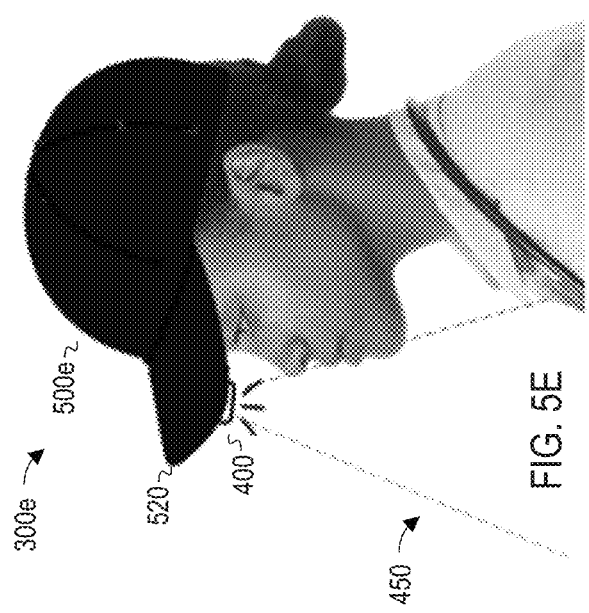
FIG. 5E illustrates the protective respirator according to another wearable embodiment.
Figure 5G:
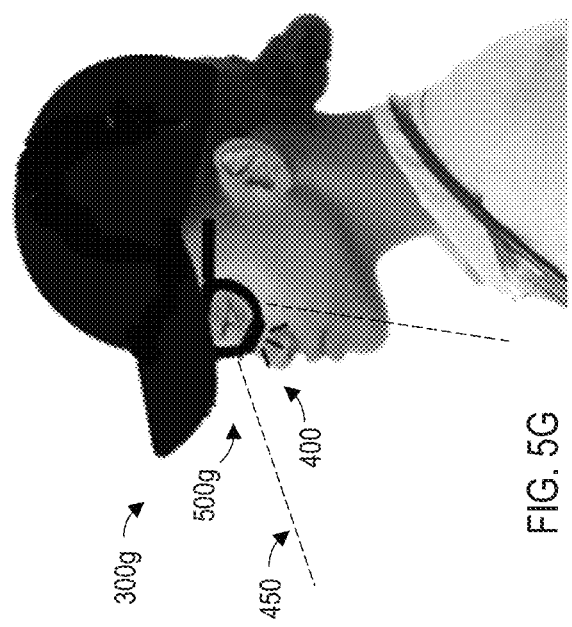
FIG. 5G illustrates the protective respirator according to another wearable embodiment.

In the embodiments of FIGS. 5B through 5D, the protective respirators 300b through 300d are realized as headwear 500b, 500c, and 500d that each include a boom 510 that extends in front of the user's face. In those embodiments, the Far UV-C radiation source(s) 400 may be incorporated in the boom 510 to emit Far UV-C radiation 450 across an area in front of the user's nose and mouth. In some of those embodiments, the Far UV-C radiation source(s) 400 may emit Far UV-C radiation 450 towards the user's face. In FIG. 5E, the protective respirator 300e is realized as a hat 500d with a brim 520. In those embodiments, the Far UV-C radiation source(s) 400 may be attached to the bottom of the brim 520 to emit Far UV-C radiation 450 across an area in front of the user's nose and mouth. In FIG. 5F, the protective respirator 300f is realized as a helmet 500f with Far UV-C radiation source(s) 400 extending out from the front to emit Far UV-C radiation 450 across an area in front of the user's nose and mouth. In the embodiment of FIG. 5G, the protective respirator 300g is realized such that the Far UV-C radiation source(s) 400 are incorporated in eyewear 500g.

In wearable embodiments, the protective respirator 300 emits Far UV-C radiation 450 through a kill zone 600 in front of the user's nose and mouth. FIGS. 6A through 6D illustrate a kill zone 600 according to various exemplary embodiments.

Figure 6B:
FIGS. 6A and 6B illustrate a kill zone according to an exemplary embodiment.
Figure 6A:
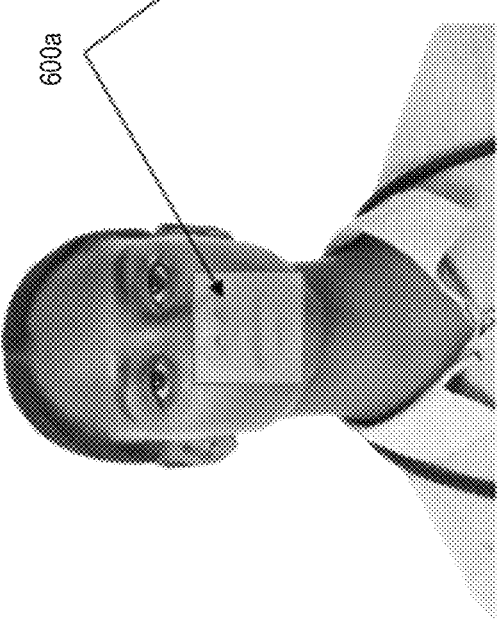
Figure 6D:
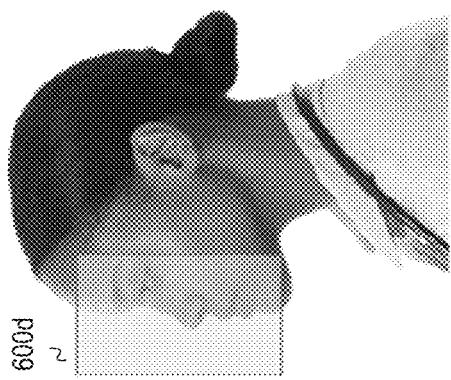
FIG. 6D illustrates a kill zone according to another exemplary embodiment.
Figure 6C:
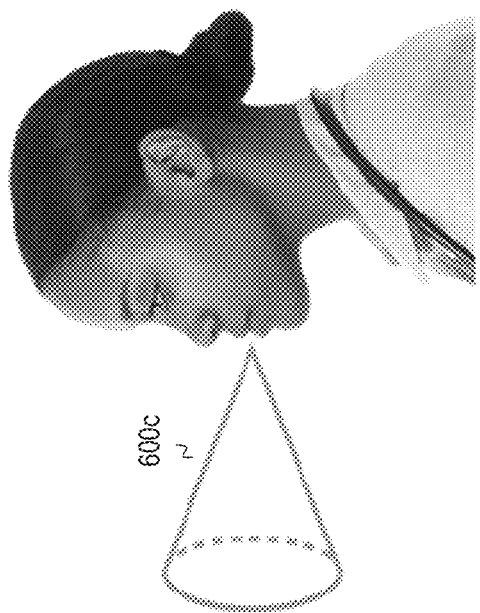
FIG. 6C illustrates a kill zone according to another exemplary embodiment.

In some wearable embodiments, such as the pendant 500a and the glasses 500g, the protective respirator 300 is configured such that the Far UV-C radiation source(s) 400 emit the Far UV-C radiation 450 away from the user's skin and eyes. As shown in FIGS. 6A and 6B, the kill zone 600a is a volume of air that includes a plane (measuring, for example, approximately 10 cm by 10 cm) in front of the user's mouth and nose. In the embodiment of FIG. 6C, the kill zone 600b includes a cone-shaped volume of air with an apex in front of the user's mouth.

In other embodiments, the protective respirator 300 may be configured such that some Far UV-C radiation is absorbed by the user's skin or eyes. In the embodiment of FIG. 6D, the kill zone 600d is a volume that includes the user's mouth, nose, and, in some embodiments, the user's eyes.

As described above, the protective respirator 300 is configured to inactivate microbes (including microorganisms and/or virus particles such as bacteria, spores, viruses, protozoa, and/or fungi) by emitting Far UV-C radiation 450. In some embodiments, the protective respirator 300 is configured to provide a threshold probability (e.g., 90 percent, 99 percent, 99.9 percent, etc.) of killing a specific microbe travelling through the kill zone 600. The probability p of killing a specific microbe (or the proportion of those microbes killed) during irradiation depends on the fluence D of the Far UV-C radiation 450 and the susceptibility constant k of the specific microbe:

$$p = 1 - e^{-D*k}$$

Meanwhile, the fluence D of the Far UV-C radiation 450 depends on the intensity I of the Far UV-C radiation 450 along the path of that microbe and the time t that the microbe is exposed to that Far UV-C radiation 450:

$$D = \int I(t) \cdot dt$$

Briefly referring back to FIG. 5A, in embodiments where the Far UV-C radiation source 400 is a point source, the intensity I of the Far UV-C radiation 450 falls off with the inverse square of the distance from the Far UV-C source 400. Meanwhile, the time t that the microbe is exposed to depends on the velocity of the microbe and the distance d through the Far UV-C radiation 450. The longer the path of a particle through the Far UV-C radiation 450, the greater the absorbed radiation or fluence and the higher the killing of microbes within the particle. Particles passing through the longer relative distance (e.g., the distance d3 of FIG. 5A) experience longer time exposure to the Far UV-C radiation 450 than shorter relative distances (e.g., the distance d1 in FIG. 5A), which may result in receipt of higher levels of fluence D received.

Referring back to FIG. 3, in some embodiments, the controller 310 determines the required intensity I to emit Far UV-C radiation 450 to achieve the predetermined probability p (e.g., 90 percent, 99 percent, etc.) of killing the selected microbe (e.g., the SARS-CoV-2 virus). In other embodiments, the intensity I of the UV-C radiation 450 emitted by the UV-C radiation source 400 may be constant. In some of those embodiments, the controller 310 may determine the required time t that to emit that Far UV-C radiation 450 to achieve the predetermined probability p of killing that selected microbe.

In addition to the distance from the Far UV-C radiation source 400 and the distance d the microbe travels through the Far UV-C radiation 450, the required intensity I and/or time t to achieve the probability p of killing a specific microbe depends on the velocity of the microbe, which is dependent on the aerosol particle size distribution and atmospheric conditions (humidity, wind speed or local ventilation) in the kill zone 600. Therefore, in some embodiments, the protective respirator 300 collects data indicative of the atmospheric conditions in the kill zone 600.

In some embodiments, for instance, the protective respirator 300 may receive data indicative of the air temperature in the kill zone 600 (e.g., from the temperature sensor 322), the relative humidity in the kill zone 600 (e.g., from the relative humidity sensor 324), the absolute atmospheric pressure and/or changes in the atmospheric pressure in the kill zone 600 (e.g., using atmospheric pressure readings from a barometer 326), and/or the wind speed or ventilation in the kill zone 600 (e.g., using data from the wind speed sensor 328).

In wearable embodiments, the kill zone 600 includes the area in front of the user's nose and mouth. Therefore, in those wearable embodiments, the atmospheric conditions in the kill zone 600 may be highly dependent on the behavior of the user (e.g., the frequency, intensity, and amplitude of the user's respiration). Accordingly, in some embodiments, the protective respirator 300 may collect data indicative of the user's physiological condition. In some embodiments, for instance, the protective respirator 300 may receive data indicative of the activity level of the user (e.g., from the geolocation module 360 and/or the inertial measurement unit 350). In those embodiments, the controller 210 may store information indicative of the user's physiological condition (e.g., sex, weight, height, smoking status, pulmonary well-being, etc.). Together, the activity level of the user and the user's physiological condition are highly correlated with the frequency, intensity, and amplitude of the user's respiration.

In other embodiments, the protective respirator 300 may receive data indicative of the physiological condition of the user (e.g., data indicative of volumetric variations of blood circulation from the PPG sensor 382, data indicative of galvanic skin response from the GSR sensor 384, etc.), which are also highly correlated with the frequency, intensity, and amplitude of the user's respiration.

In still other embodiments, the protective respirator 300 may receive sound data (e.g., from the microphone 370) and execute a mathematical model (stored, e.g., in the memory 318) to isolate sounds indicative of the user's respiration.

In some wearable embodiments, the protective respirator 300 may be worn on the user's body in a location uniquely suited to gather data indicative of respiration. In the embodiment where the Far UV-C radiation source(s) 400 is incorporated in the pendant 500a of FIG. 5A, for example, the protective respirator 300b-300d may include an inertial measurement unit 350 that collects data indicative of the motion of the user's chest, which is highly correlated with the frequency, intensity, and amplitude of the user's respiration. In the embodiments where the Far UV-C radiation source(s) 400 is incorporated in the headwear 500b of FIG. 5B or the headset 500c or 500d of FIG. 5C or 5D, the protective respirator 300b-300d may include a PPG sensor 382 on the user's temple to measure data indicative of volumetric variations of blood circulation.

To determine the required intensity I of the Far UV-C radiation 450 (and/or the required amount of time t emitting Far UV-C radiation 450) to achieve the predetermined probability p to kill the selected microbe, the controller 310 uses a mathematical model (stored, for example, in the memory 318) developed based on laboratory experiments and computational fluid dynamics.

Figure 7A:
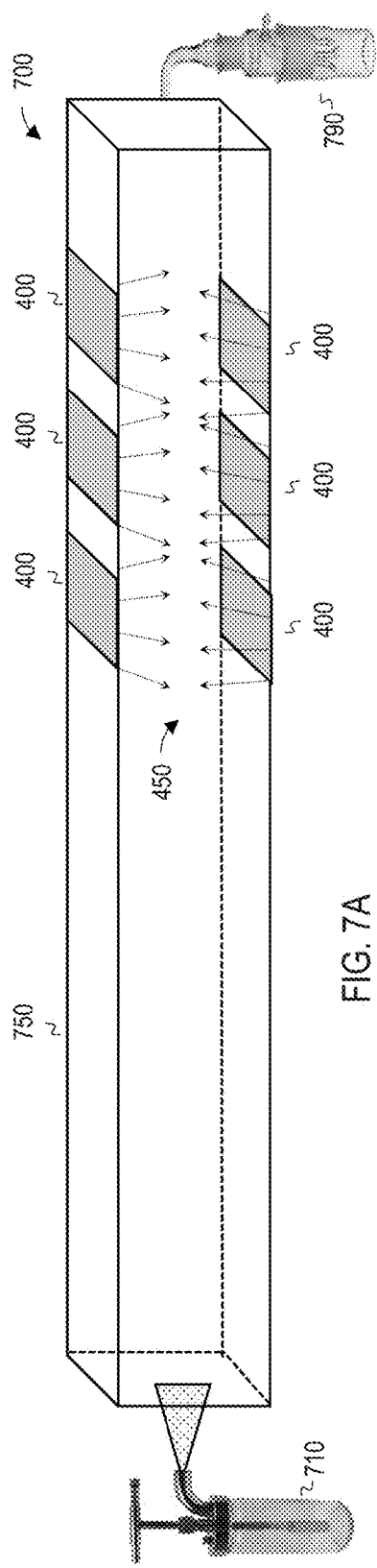
FIG. 7A illustrates an example laboratory experiment.

FIG. 7A illustrates an example laboratory experiment 700 to measure the intrinsic kinetics of the inactivation response of aerosolized viruses.

In the example laboratory experiment 700, aerosolized viruses are introduced into a quartz channel 750 using a nebulizer 710. The quartz channel 750 includes a number of Far UV-C radiation sources 400 that emit Far UV-C radiation 450. The aerosolized viruses are exposed to the Far UV-C radiation 450 as they pass through the quartz channel 750. Samples are collected at the output of the quartz channel 750 using a bioaerosol sampler 790. Those samples are then analyzed to determine the inactivation response of the aerosolized viruses that are exposed to the Far UV-C irradiation 450.

To determine the inactivation response of known viruses, the laboratory experiments are conducted using biological surrogates for those pathogens. For example, experiments are conducted using phages that have the ability to infect bacteria but no ability to affect human tissues. To determine the inactivation response of coronaviruses, for instance, phages are selected that have responses to UV radiation that are similar to those coronaviruses. For instance, the T1 and T1UV phage, the Φ6 phage, the Qβ phage, and the mouse hepatitis virus (MHV) all have similar log-linear (first order) behavior and are all slightly conservative for coronaviruses.

Having measured the intrinsic kinetics of the inactivation responses of known pathogens using those laboratory experiments, the inactivation responses of those known pathogens are then simulated by a computer model using computational fluid dynamics.

Figure 7B:
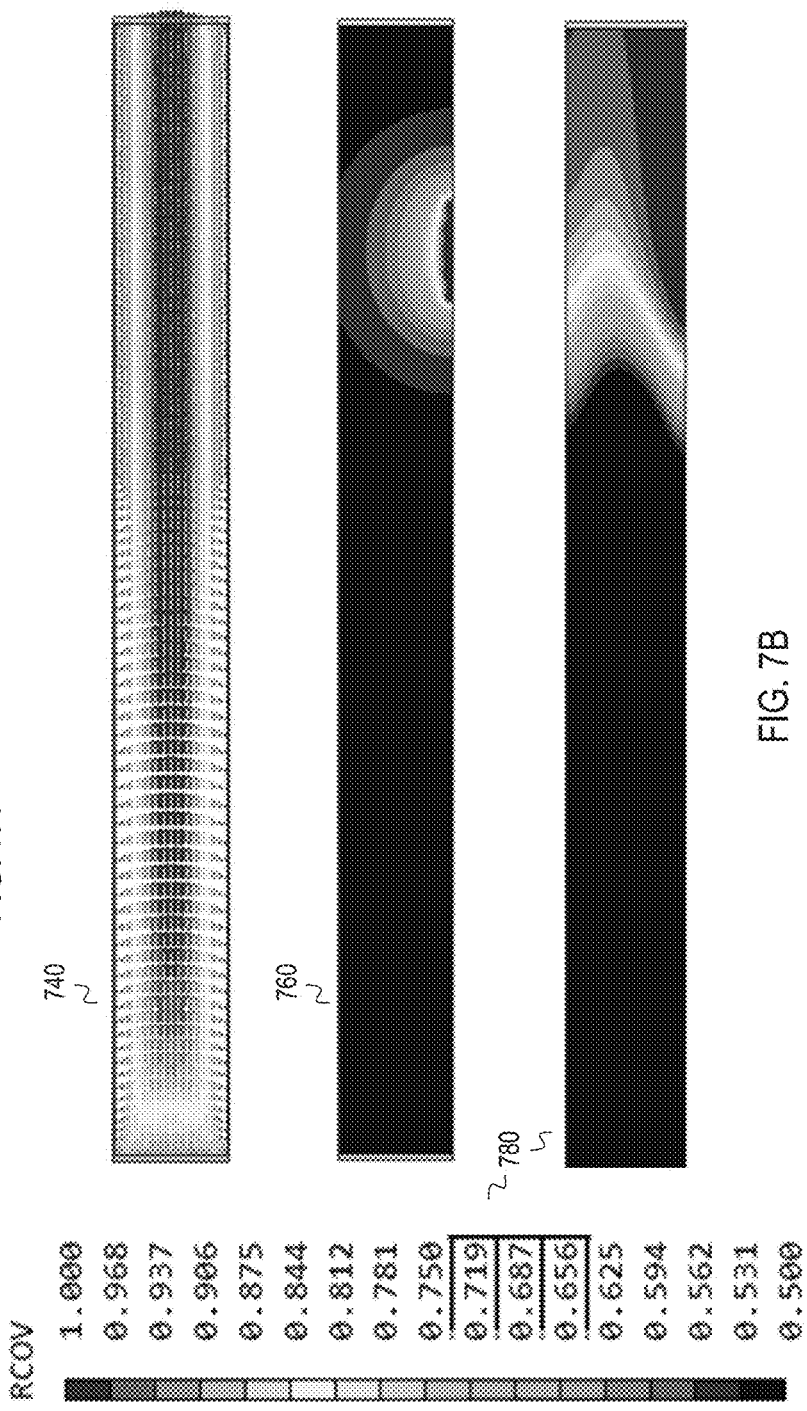
FIG. 7B illustrates a computer simulation of the inactivation response during the experiment of FIG. 7A.

FIG. 7B illustrates a computer simulation of the inactivation response during the experiment 700. Heat map 740 is a map of the velocity vector field through the quartz channel 750. Image 760 is a map of the fluence rate contours of one of the Far UV-C radiation sources 400. Integrating that velocity field and the fluence rate of the Far UV-C radiation source(s) 400 with the kinetics of inactivation for a specific pathogen enables the system to develop a mathematical model predicting the inactivation response of the specific pathogen, as shown in Image 780, as it passes through the channel 750.

Figure 8A:
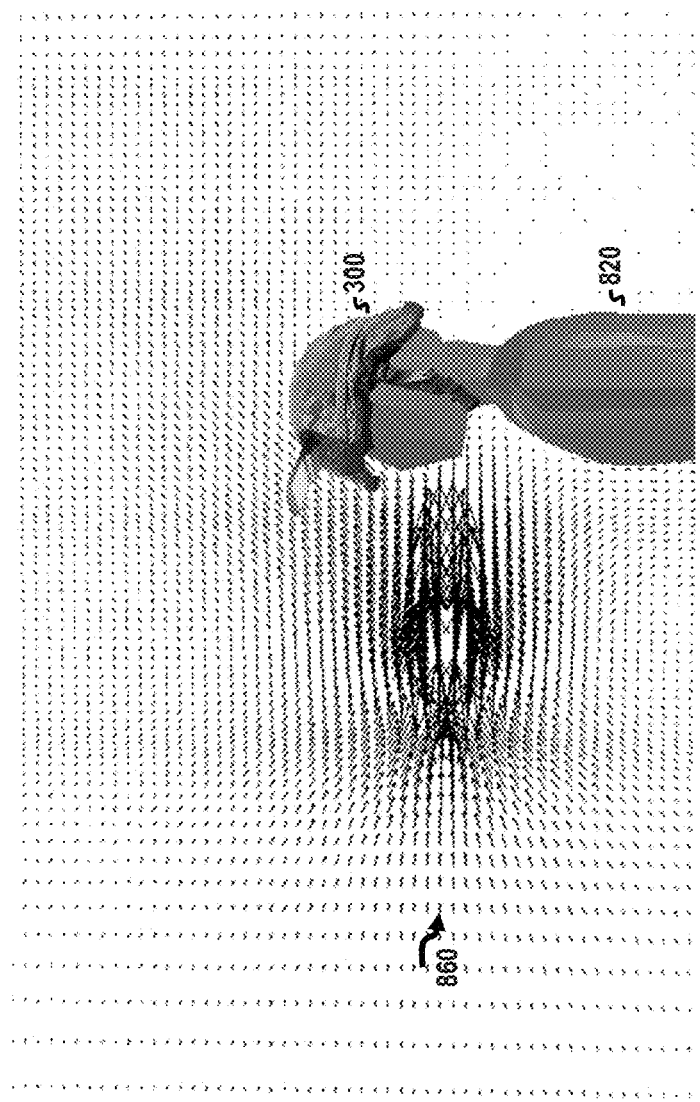
FIGS. 8A, 8B, and 8C illustrate simulations using computational fluid dynamics according to exemplary embodiments.
Figure 8B:
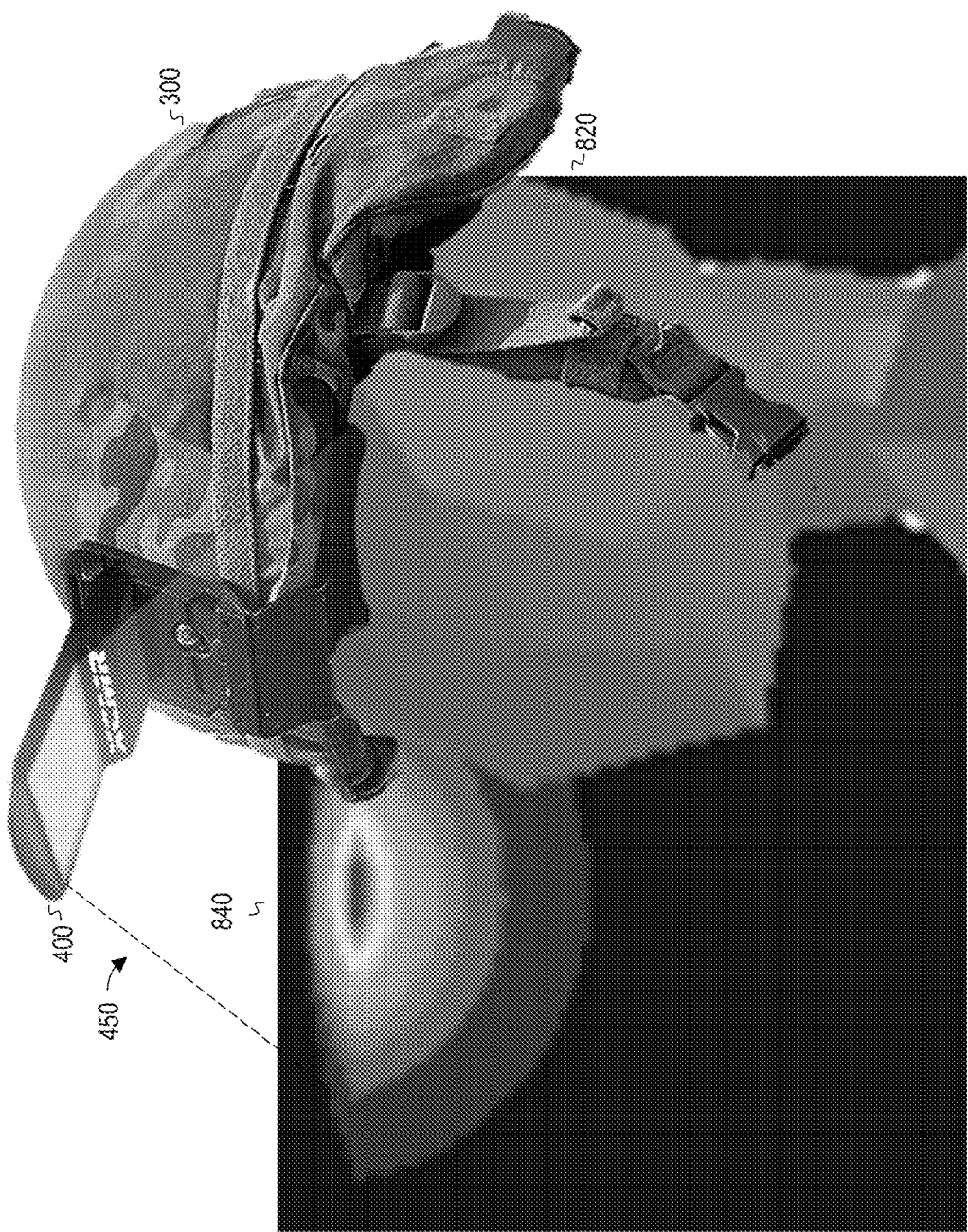
Figure 8C:
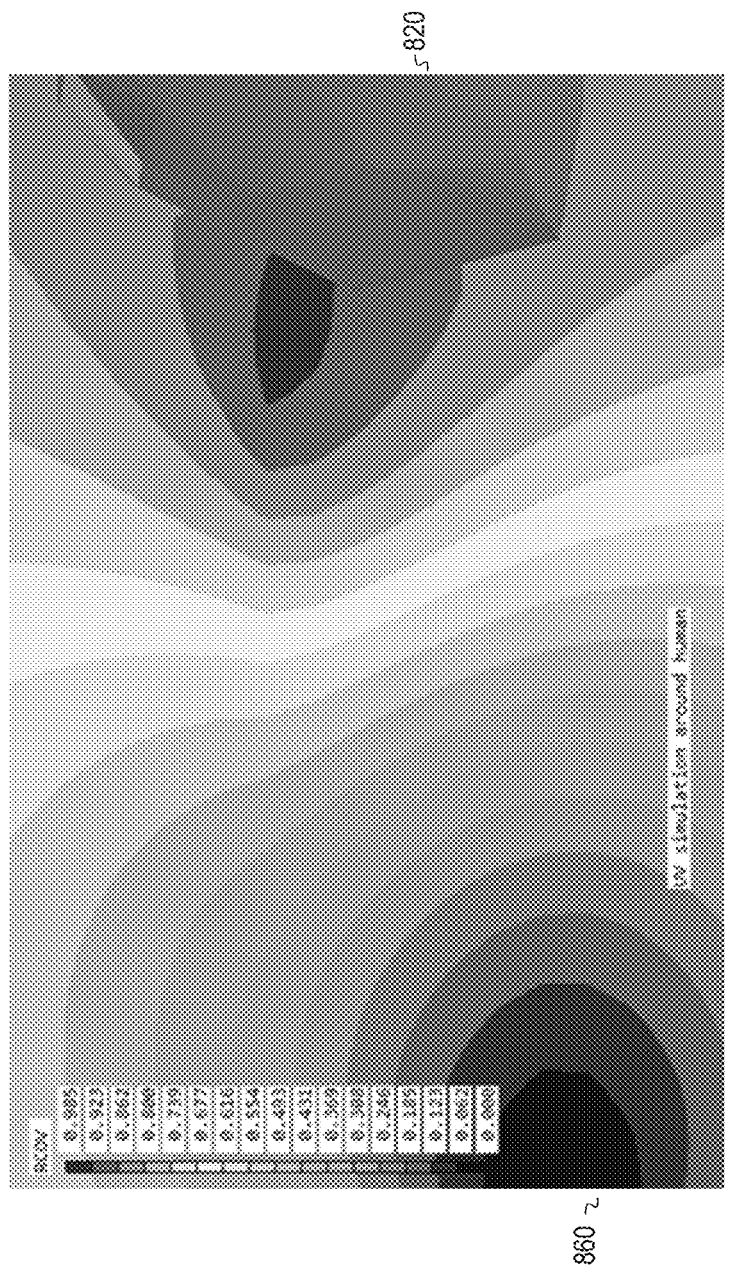

FIGS. 8A through 8C further illustrate simulations using computational fluid dynamics that inform the model executed by the controller 310 of the protective respirator 300 to determine the required intensity I of the Far UV-C radiation 450 (and/or the required amount of time t emitting Far UV-C radiation 450) to achieve the predetermined probability p of killing the selected microbe.

FIG. 8A is a simulation of the airflow 810 in a room that includes a user 820 wearing a protective respirator 300 and a person 860 (not shown) emitting viruses toward the user 820 (e.g., by coughing or breathing). FIG. 8B shows a heat map 840 of a simulated fluence rate of the Far UV-C radiation 450 emitted by the Far UV-C radiation source(s) 400 of the protective respirator 300 worn by the user 820. Using computational fluid dynamics, the system combines the velocity field in the environment of the user 820 (shown in FIG. 8A), the fluence rate of the Far UV-C radiation 450 emitted by the Far UV-C radiation source(s) 400 of the protective respirator 300 (shown in FIG. 8B), and the inherent kinetics of inactivation of a specific pathogen (identified using laboratory experiments, for example as shown in FIG. 7A) to develop a mathematical model of the inactivation response of the specific pathogen through the kill zone 600 of the protective respirator 300. FIG. 8C is a heat map of the predicted inactivation response, as determined by the mathematical model, around the user 820 of the protective respirator 300 in FIGS. 8A and 8B. Using that mathematical model (and, in some embodiments, data indicative of the atmospheric conditions in the kill zone 600), the controller 310 determines the required intensity I of Far UV-C radiation 450 (and/or the required amount of time t emitting Far UV-C radiation 450) to deliver the required fluence D to achieve a predetermined probability p of killing a specific microbe (e.g., SARS-CoV-2) as it passes through the kill zone 600.

As described above, in wearable embodiments, the protective respirator 300 protects the user (and reduces the likelihood of the user infecting others nearby) by emitting Far UV-C radiation 450 through the kill zone 600 in front of the user's mouth and nose. In some embodiments, the protective respirator 300 also protects the user from being exposed to an unsafe amount of Far UV-C radiation.

In some wearable embodiments, the protective respirator 300 is realized such that the Far UV-C radiation source(s) 400 emit Far UV-C radiation 450 away from the user (for example, as shown in FIG. 5C) through a kill zone 600 in front of the user's mouth and nose (e.g., as shown in FIGS. 6A through 6C). In other wearable embodiments, the protective respirator 300 is realized such that the Far UV-C radiation source(s) 400 emit Far UV-C radiation 450 across a kill zone 600 in front of the user's nose and mouth (e.g., as shown in FIGS. 6A-6B) without emitting Far UV-C radiation 450 towards the user's skin or eyes (e.g., as shown in FIG. 5A). In some embodiments, however, some of the Far UV-C radiation 450 emitted by one or more Far UV-C radiation source(s) 400 may be absorbed by the user's skin or eyes. Therefore, in some of those embodiments, the controller 310 may be configured to limit the amount of Far UV-C radiation 450 emitted towards the user.

Briefly referring back to FIG. 3, in some embodiments, the controller 310 receives data indicative of the distance between one or more of the Far UV-C radiation source(s) 400 and the user (e.g., from the distance sensor 330). Using that distance and the intensity I of the Far UV-C radiation 450 emitted towards the user, the controller 310 can determine the fluence of the Far UV-C radiation 450 at the location of the user's skin or eyes. In some of those embodiments, the controller 310 may determine the total dosage of Far UV-C radiation 450 over time and adjust the intensity I of the Far UV-C radiation 450 emitted towards the user (or the time t that the Far UV-C radiation 450 is emitted towards the user) to limit the dosage of Far UV-C radiation 450 absorbed by the user's skin and/or eyes. For instance, the controller 310 may reduce the intensity I of the Far UV-C radiation 450 (or the time t that the Far UV-C radiation 450 is emitted) to prevent the protective respirator 300 from emitting more than the threshold limit value of Far UV-C radiation 450 towards the user over a predetermined time period (e.g., 8 hours) or a time period, specified by the user, that the user expects to wear the protective respirator 300.

In embodiments where the protective respirator 300 includes more than one Far UV-C radiation source 400, the controller 310 may use data from the distance sensor 330 to determine which of the Far UV-C radiation sources 400 are emitting Far UV-C radiation 450 towards the user's skin or eyes (and the distance between each of those Far UV-C radiation sources 400) and limit the intensity I of the Far UV-C radiation 450 (and/or the time t that the Far UV-C radiation 450 is emitted) over the predetermined or user-specified time period.

In embodiments where the power supply 390 is a rechargeable battery, the controller 310 may also monitor the amount of charge stored by the battery over time and limit the intensity I of the Far UV-C radiation 450 (and/or the time t that the Far UV-C radiation 450 is emitted) so that the protective respirator 300 emits Far UV-C radiation 450 over a predetermined time period or a time period, specified by the user, that the user expects to wear the protective respirator 300.

FIG. 9 is a diagram of a network environment 900 according to exemplary embodiments. As shown in FIG. 9, the protective respirator 300 may communicate with a server 920 (e.g., using the communications module 320) over one or more wide area networks 950 such as the interne. Additionally or alternatively, the protective respirator 300 may pair with a personal electronic device 940 (e.g., a smartphone) using a direct, wireless communications protocol (e.g., Bluetooth). In those embodiments, the protective respirator 300 may communicate with the server 920 via the personal electronic device 940. In some of those embodiments, the personal electronic device 940 may also be paired with an activity tracker 960 (e.g., a fitness tracker, wristband, smartwatch, etc.).

By communicating with the server 920, the protective respirator 300 is able to receive the mathematical model (developed using computational fluid dynamics and the intrinsic kinetics of inactivation identified in laboratory experiments as described above) used by the controller 310 to determine the required intensity I of Far UV-C radiation 450 (and/or the required amount of time t emitting Far UV-C radiation 450) to deliver the required fluence D to achieve a predetermined probability p of killing a specific microbe (e.g., SARS-CoV-2) as it passes through the kill zone 600.

As described above with reference to FIG. 3, in some embodiments, the required intensity I of Far UV-C radiation 450 (and/or the required amount of time t emitting Far UV-C radiation 450) is determined using data indicative of the atmospheric conditions surrounding the protective respirator 300 and/or the user's physiological condition (e.g., respiration). In the embodiment of FIG. 3, the protective respirator 300 includes atmospheric sensors 340, an inertial measurement unit 350, a geolocation module 360, a microphone 370, and/or physiological sensors 380. In other embodiments, however, the personal electronic device 940 and/or activity tracker 960 may include some or all of those sensors. In some of those embodiments, the protective respirator 300 may receive data indicative of the atmospheric conditions and/or the user's physiological condition from the personal electronic device 940 and/or activity tracker 960.

As shown in FIG. 9, in some embodiments, the protective respirator 300 may receive data indicative of the atmospheric conditions from other sources. For instance, the protective respirator 300 may receive data indicative of the atmospheric conditions from a location beacon 980 (e.g., indicating that the protective respirator 300 is located in a building with a specific ventilation system providing a specific rate of air exchange).

In some embodiments, each protective respirator 300 is configured to communicate with other protective respirators 300 (e.g., via Bluetooth, a mesh network, a local area network, a cell network, etc.). In some of those embodiments, each protective respirator 300 may determine the required intensity I of Far UV-C radiation 450 (and/or the required amount of time t emitting Far UV-C radiation 450)—as dictated by the mathematical model—for the protective respirators 300 to collectively achieve the predetermined probability p of killing the specified microbe in the kill zones 600 of each user.

In some embodiments, the protective respirator 300 may receive data indicative of the atmospheric conditions from the server 920. For instance, one atmospheric condition that may be relevant for determining the required intensity I of Far UV-C radiation 450 (and/or the required amount of time t emitting Far UV-C radiation 450) is whether the protective respirator 300 is indoors or outdoors. Therefore, in some embodiments, the controller 310 may output the geographic location of the protective respirator 300 (determined, for example, by the geolocation module 360) and the server 920 may determine, based on that location, whether the protective respirator 300 is indoors or outdoors. To determine whether the protective respirator 300 is indoors or outdoors, the server 920 may store a two-dimensional map of building locations and determine whether the location of the protective respirator 300 is within one of the buildings. Additionally, the server 920 may store a topographical map and determine whether the altitude of the protective respirator 300 is above or below ground level (indicating that the user is on an upper floor or in a basement).

Figure 10:
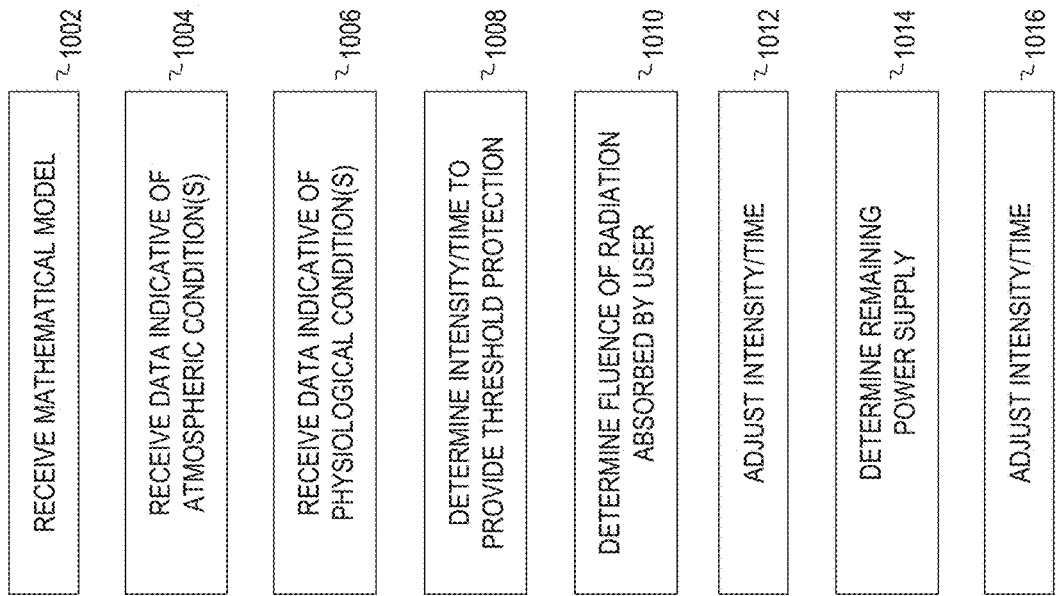
FIG. 10 is a flow chart illustrating a process to inactivate microbes (e.g., microorganisms and/or virus particles such as bacteria, spores, viruses, protozoa, and/or fungi) according to exemplary embodiments.

FIG. 10 is a flow chart illustrating a process 1000 performed by the protective respirator 300 to inactivate microbes (e.g., microorganisms and/or virus particles such as bacteria, spores, viruses, protozoa, and/or fungi) according to exemplary embodiments. As described in detail above, the protective respirator 300 inactivates microbes by emitting Far UV-C radiation 450. In some embodiments, the protective respirator 300 is configured to emit Far UV-C radiation 450 having sufficient intensity I for a sufficient time t to provide a threshold probability (e.g., 90 percent, 99 percent, of killing a specific microbe (e.g., the SARS-CoV-2 virus) travelling through the kill zone 600.

To determine the required intensity I of the Far UV-C radiation 450 and/or the required time t to achieve the threshold probability of killing the selected microbe, the protective respirator 300 stores a mathematical model in memory 318 in step 1002. As described above, the mathematical model may be developed by using computational fluid dynamics to combine the velocity fields in various simulated environments, the fluence rate of the Far UV-C radiation 450 emitted by the Far UV-C radiation source(s) 400, and the intrinsic kinetics of the inactivation response of the selected microbe (identified in laboratory experiments). As described above with reference to FIG. 9, in some network-connected embodiments, the mathematical model may be received from a server 920. In other embodiments, the mathematical model may be stored in memory 318 at the time of manufacturing.

As described above, the required intensity I (and/or the required time t) to achieve the threshold probability p of killing the specific microbe depends on the velocity of the microbe, which may be dependent on the atmospheric conditions in the kill zone 600. Therefore, in some embodiments, the protective respirator 300 receives data indicative of the atmospheric conditions in the environment surrounding the protective respirator 300 in step 1004. As described above with reference to FIG. 9, the data indicative of the atmospheric conditions may be received from a server 920, a personal electronic device 940, a location beacon 980, etc. As described above with reference to FIG. 3, the data indicative of the atmospheric conditions may be received from one or more atmospheric sensors 340 (incorporated in the protective respirator 300, the personal electronic device 940, etc.).

As described above, atmospheric conditions in the kill zone 600 may be dependent on the physiological condition of the user. Therefore, in some embodiments, the protective respirator 300 receives data indicative of the physiological condition of the user in step 1006. As described above with reference to FIG. 9, the data indicative of the physiological condition of the user may be received from a personal electronic device 940, an activity tracker 960, etc. As described above with reference to FIG. 3, the data indicative of the physiological condition of the user may be received from an inertial measurement unit 350, a geolocation module 360, one or more physiological sensors 380, etc. (incorporated in the protective respirator 300, the personal electronic device 940, the activity tracker 960, etc.).

The controller 310 determines the required intensity I (and/or the required time t) to achieve the threshold probability p of killing the specific microbe in step 1008.

In some embodiments, the protective respirator 300 is configured such that one or more of the Far UV-C radiation source(s) 400 emit Far UV-C radiation 450 toward the user's skin and/or eyes. Therefore, in some embodiments, the controller 310 determines the fluence rate D of the Far UV-C radiation 450 absorbed by the user in step 1010 and adjusts the intensity I of the Far UV-C radiation 450 emitted by one or more of the Far UV-C radiation source(s) 400 and/or the time t that those one or more of the Far UV-C radiation source(s) 400 emit Far UV-C radiation 450 in step 1012 to prevent the fluence of the Far UV-C radiation 450 absorbed by the user's skin or eyes from exceeding a threshold limit value over a predetermined time period (e.g., 8 hours) or a time period, specified by the user, that the user expects to wear the protective respirator 300.

In some embodiments, the power supply 390 of the protective respirator 300 is a rechargeable battery. Therefore, in some embodiments, the controller 310 determines the amount of charge remaining in the power supply 390 in step 1014 and adjusts the intensity I of the Far UV-C radiation 450 (and/or the time t that the Far UV-C radiation 450 is emitted) so that the protective respirator 300 emits Far UV-C radiation 450 over an entire predetermined time period (e.g., 8 hours) or a time period, specified by the user, that the user expects to wear the protective respirator 300.

As described above, in some embodiments, the protective respirator 300 may be wearable. However, the protective respirator 300 is not so limited.

FIG. 11 illustrates the protective respirator 300 according to a portable embodiment. In the portable embodiment of FIG. 11, the protective respirator 300 is realized as a wand 1100 that includes one or more Far UV-C radiation source(s) 400 that emit Far UV-C radiation 450.

FIG. 12 illustrates the protective respirator 300 according to a stationary embodiment. In the embodiment of FIG. 12, the protective respirator 300 is realized as an object 1200 (in this example, a table tamp) that includes one or more Far UV-C radiation source(s) 400 that emit Far UV-C radiation 450.

While preferred embodiments have been set forth above, those skilled in the art who have reviewed the present disclosure will readily appreciate that other embodiments can be realized within the scope of the invention. Therefore, the present invention should be construed as limited only by any appended claims.

What is claimed is:

1. A protective respirator that utilizes ultraviolet (UV) irradiation to deactivate pathogens in a kill zone in front of a mouth and nose of a user, the protective respirator comprising:
   a power source;
   one or more Far UV-C radiation sources that emits Far UV-C radiation through the kill zone; and
   a controller that:
      receives data indicative of one or more physiological conditions of the user; and
      determines a required intensity of the Far UV-C radiation or a required time to emit the Far UV-C radiation to provide a predetermined probability of killing a microbe traveling through the kill zone based at least in part on the data indicative of the one or more physiological conditions of the user.

2. The protective respirator of claim 1, wherein the Far UV-C radiation has a wavelength centered around 222 nanometers (nm).

3. The protective respirator of claim 1, wherein the microbe is a virus.

4. The protective respirator of claim 1, wherein:
   the required intensity or time is determined further based on one or more atmospheric conditions; and
   the controller receives data indicative of the one or more atmospheric conditions.

5. The protective respirator of claim 4, wherein the data indicative of the one or more atmospheric conditions is received from a server, a personal electronic device, or a location beacon.

6. The protective respirator of claim 4, wherein the data indicative of the one or more atmospheric conditions is determined by one or more atmospheric sensors.

7. The protective respirator of claim 1, further comprising:
a communications module that communicates with an additional protective respirator having an associated kill zone in front of an additional user,
wherein the controller determines the required intensity or time for each of the protective respirator and the additional protective respirator to collectively provide the predetermined probability of killing the microbe in each of the kill zone of the protective respirator and the associated kill zone of the additional protective respirator.

8. The protective respirator of claim 1, wherein the data indicative of the one or more physiological conditions is received from a personal electronic device or a fitness tracker.

9. The protective respirator of claim 1, wherein the data indicative of the one or more physiological conditions is determined by an inertial measurement unit, a geolocation module, or one or more physiological sensors.

10. The protective respirator of claim 1, wherein the one or more Far UV-C radiation sources emit the Far UV-C radiation away from the user.

11. The protective respirator of claim 1, wherein the one or more Far UV-C radiation sources emit the Far UV-C radiation through the kill zone in a direction that does not intersect with the skin or eyes of the user.

12. The protective respirator of claim 1, wherein the controller:
estimates the fluence of Far UV-C radiation at the skin or eyes of the user over time; and
adjusts the Far UV-C radiation emitted by the one or more Far UV-C radiation sources in response to the determination.

13. The protective respirator of claim 1, wherein the controller:
monitors a charge level of the power source over time; and
adjusts the Far UV-C radiation emitted by the one or more Far UV-C radiation sources in response to the determination.

14. A method of utilizing ultraviolet (UV) irradiation, by a protective respirator, to deactivate pathogens in a kill zone in front of a mouth and nose of a user, the protective respirator comprising a power source, a controller, and one or more Far UV-C radiation sources, the method comprising:
receiving, by the controller, data indicative of one or more physiological conditions of the user;
determining, by the controller, a required intensity of Far UV-C radiation or a required time to emit the Far UV-C radiation to provide a predetermined probability of killing a microbe traveling through the kill zone based at least in part on the one or more physiological conditions of the user; and
emitting Far UV-C radiation, by the one or more Far UV-C radiation sources, through the kill zone in front of the mouth and nose of the user.

15. The method of claim 14, further comprising:
receiving data indicative of the one or more atmospheric conditions,
wherein the required intensity or time is determined further based on the data indicative of the one or more atmospheric conditions.

16. The method of claim 15, wherein the data indicative of the one or more atmospheric conditions is determined by one or more atmospheric sensors.

17. The method of claim 14, wherein determining the required intensity or time comprises determining the required intensity or time for each of a plurality of protective respirators to collectively provide the predetermined probability of killing the microbe in each of a plurality of kill zones in front of the mouth and nose of a plurality of users.

18. The method of claim 14, wherein the data indicative of the one or more physiological conditions is received from a personal electronic device or a fitness tracker.

19. The method of claim 14, wherein the data indicative of the one or more physiological conditions is determined by an inertial measurement unit, a geolocation module, or one or more physiological sensors.

* * * * *